(12) United States Patent
Aylwin et al.

(10) Patent No.: US 6,652,880 B1
(45) Date of Patent: Nov. 25, 2003

(54) ORAL PHARMACEUTICAL COMPOSITIONS CONTAINING LONG-CHAIN TRIGLYCERIDES AND LIPHOPHILIC SURFACTANTS

(75) Inventors: Elizabeth Anne Aylwin, Swindon (GB); Susan Banbury, Cheltenham (GB); Josephine Joan Christine Ferdinando, Tadley (GB); Henrik de Nijs, Oss (NL)

(73) Assignee: R.P. Scherer Technologies, Inc., Paradise Valley, NV (US)

( * ) Notice: Subject to any disclaimer, the term of this patent is extended or adjusted under 35 U.S.C. 154(b) by 0 days.

(21) Appl. No.: 09/914,576

(22) PCT Filed: Mar. 29, 2000

(86) PCT No.: PCT/US00/08426
§ 371 (c)(1), (2), (4) Date: Dec. 21, 2001

(87) PCT Pub. No.: WO00/59482
PCT Pub. Date: Oct. 12, 2000

(30) Foreign Application Priority Data

Apr. 1, 1999 (GB) ............................................. 9907715

(51) Int. Cl.$^7$ ............................. A61K 9/48; A61K 9/66
(52) U.S. Cl. ........................ 424/455; 424/451; 424/452; 424/456; 514/970; 514/785; 514/786
(58) Field of Search ................................. 424/451, 452, 424/455, 456

(56) References Cited

U.S. PATENT DOCUMENTS 4,083,973 A  4/1978  van der Vies ............... 424/239
4,098,802 A  7/1978  van der Vies ............ 260/397.4
4,147,783 A  4/1979  van der Vies ................ 424/243
4,220,599 A  9/1980  van der Vies ............ 260/397.4
5,532,002 A  7/1996  Story .......................... 424/456
5,645,856 A  7/1997  Lacy et al. .................. 424/455
5,738,871 A  4/1998  Story .......................... 424/451

FOREIGN PATENT DOCUMENTS

WO  95/24893  9/1995
WO  97/40823  11/1997
WO  99/06024  2/1999
WO  00/59512  10/2000

OTHER PUBLICATIONS

*International Journal of Pharmaceutics*, 24 (1985) 173–184; Entitled: "The effect of drug lipophilicity and lipid vehicles on the lymphatic absorption of various testosterone esters" to Noguchi et al.

Primary Examiner—James M. Spear
(74) Attorney, Agent, or Firm—Dobald O. Nickey; Andrew G. Rozycki

(57) ABSTRACT

This invention is directed to pharmaceutical compositions for oral administration, wherein the drug or active ingredient is known to have stability problems associated with the use of free fatty acids. The compositions of the invention enhance the solubility of such compounds and improve the storage stability thereof and can be advantageously used in soft-gel and hard-shell capsular formulations. The liquid pharmaceutical compositions, according to the present invention, have a drug dissolved in a liquid vehicle. The liquid vehicle comprising a glyceride of a long chain fatty acid and a lypophilic surfactant having an HLB of less than ten. The composition, according to the invention, is also substantially free of free fatty acids.

18 Claims, No Drawings

ORAL PHARMACEUTICAL COMPOSITIONS CONTAINING LONG-CHAIN TRIGLYCERIDES AND LIPHOPHILIC SURFACTANTS

RELATED APPLICATIONS

This application is a national phase filing under 35 U.S.C. 371 of International Application No. PCT/US00/08426 (WO 00/59482) filed Mar. 29, 2000, which claims the benefit of priority to Great Britain Application No. 9907715.8 filed Apr. 1, 1999.

FIELD OF THE INVENTION

The invention relates to pharmaceutical compositions for oral administration. In particular, the invention relates to liquid pharmaceutical compositions suitable for softgel encapsulation.

BACKGROUND OF THE INVENTION

A number of drugs are known to require formulation in the presence of fatty acids, such as oleic acid, to provide optimum conditions for bioavailability. For example, long-chain fatty acids can be predisposed for lymphatic absorption, and therefore, are useful in pharmaceutical formulations in which the lymphatic system is the desired target site for the active ingredient. One of the problems associated with the formulations containing fatty acids is that chemical instability can arise due to their acidic nature and the presence of reactive carboxyl groups. Esterification can occur with drug molecules containing alcohol groups or transesterification of ester molecules.

In the past, this problem has been solved by continuing to use free fatty acids in formulations which are encapsulated in softgel capsules and storing the capsules under refrigerated conditions to reduce the rate of reaction between the drug and fatty acids. However, where the drug is not sufficiently soluble in the formulation, cold storage methods result in crystallization which in turn necessitates equilibrating the capsules at room temperature to ensure crystal dissolution prior to consumption. Accordingly, complex storage regimens are required throughout the supply chain for the use of such formulations.

Lacy et al. in Patent Cooperation Treaty WO 95/24893 published Sep. 21, 1995 discloses a carrier system for a hydrophobic drug which comprises a digestible oil and a pharmaceutically acceptable surfactant for dispersing the oil in vivo upon administration of the carrier system, the surfactant comprising a hydrophilic surfactant component which does not substantially inhibit the lipolysis of the digestible oil, and a lipophilic surfactant component which substantially reduces the inhibitory effect of the hydrophilic surfactant. Suitable digestible oils are complete or partial esters of medium chain ($C_8$–$C_{12}$) or long-chain ($C_{14}$–$C_{22}$) fatty acids with low molecular weight (up to $C_6$) mono-, di- or polyhydric alcohols. Medium chain length triglycerides or long chain tri- and diglyceride mixtures which may contain monoglycerides are particularly preferred. Fractionated coconut oil is a preferred oil.

The lipophilic surfactants used include fatty acids; mono- and/or diglycerides of fatty acids; acetic, succinic, lactic, citric and/or tartaric esters of mono and/or diglycerides of fatty acids; propylene glycol mono- and/or di-esters of fatty acids; polyglycerol esters of fatty acids; castor oil ethoxylates; acid and ester ethoxylates; and sorbitan esters of fatty acids.

The hydrophilic surfactants used have a hydrophilic/lipophilic balance (HLB) value greater than 10 and include phospholipid; polyoxyethylene sorbitan fatty acid derivatives; castor oil or hydrogenated castor oil ethoxylates; fatty acid ethoxylates; alcohol ethoxylates; polyoxyethylene, polyoxypropylene co-polymers and block co-polymers; anionic surfactants and alkylphenol surfactants.

The formulations may contain ethanol as a co-solvent and formulations containing up to 15% by weight ethanol are disclosed.

Perry et al. in Patent Cooperation Treat WO 97/40823 published Nov. 6, 1997 discloses a pharmaceutical composition comprising a hydrophobic drug; a digestible oil selected from triglycerides or propylene glycol esters of medium chain length ($C_8$–$C_{12}$) and/or long chain length ($C_{13}$–$C_{22}$) fatty acids; propylene glycol monolaurate (lauroglycol), a lipophilic surfactant which comprises a glyceride of a $C_5$ to $C_{10}$ fatty acid; and a hydrophilic surfactant which is a polyoxyethylene hydrogenated castor oil, wherein the digestible oil is present in an amount in the range from 3.0 to 12.0% by weight of the composition and the weight ratio of hydrophilic surfactant to lipophilic surfactant is in the range of 1:1.5 to 1:2.5. The formulations may contain ethanol as a co-solvent for the drug and formulations containing 15–25% by weight ethanol are disclosed.

There still exists the need for pharmaceutical compositions having improved stability which promote systemic absorption.

SUMMARY OF THE INVENTION

The invention discloses a liquid pharmaceutical composition wherein the active ingredient is dissolved in a liquid vehicle comprising a combination of long chain glycerides and lipophilic surfactant. The composition according to the invention are stable and promote systemic absorption and can be used for oral formulations containing drugs or active ingredients susceptible to the adverse affects of carboxyl groups in carrier ingredients. The invention is particularly useful for oral formulations containing testosterone undecanoate (also referred to as TU).

According to the invention there is provided a liquid pharmaceutical composition comprising a drug dissolved in a liquid vehicle, the liquid vehicle comprising:

a) a glyceride of a long chain fatty acid having a chain containing from 14 to 22 carbon atoms and is present in an amount from about 15% to about 70% by weight, preferably from about 15% to about 60% by weight of said liquid vehicle;

b) a lipophilic surfactant having an HLB of less than 10 and present in an amount of from about 30% to about 60% by weight of said liquid vehicle.

The composition according to the invention contains a liquid vehicle which is substantially devoid of free fatty acids and contains less than 10% by weight ethanol.

The composition can further comprise a hydrophilic surfactant, which can be present in an amount of from about 0% to about 35% by weight of the liquid vehicle.

In one embodiment of the invention, there is provided a liquid pharmaceutical composition for oral administration having testosterone undecanoate dissolved in a liquid vehicle, the liquid vehicle consisting essentially of:

a) a glyceride of a long chain fatty acid having a chain containing from 14 to 22 carbon atoms; and b) lauroglycol.

It has now been found that the stability problem associated with free fatty acids can be avoided by the use of glycerides in which the fatty acids are esterified with glycerol to form a neutral compound which is less reactive. Thus, the invention minimizes or excludes the use of free fatty acids in the compositions.

Suitable glycerides for use in the invention are mono-, di- and triglycerides. Preferred glycerides are triglycerides, as they contain the highest fatty acid content. Long chain glycerides can liberate long chain fatty acids following lipolysis in the gastrointestinal tract. The long chain triglycerides are desirable to promote lymphatic absorption in a manner similar to the respective fatty acids. See, for example, Henk de Nijs, *Acta Technol.*, 33(4) pp.163–168 (1987), which discusses the enhancement of lymphatic absorption by using triglycerides and different absorption mechanisms involved with long and medium chain fatty acids.

In the present invention, the presence of the lipophilic surfactant, and optionally the additional hydrophilic surfactant, enhances the solubility of drugs in the liquid triglyceride carrier while maintaining the stability of the composition.

The invention is particularly useful in pharmaceutical compositions containing drugs, i.e., active ingredients, compounds, pro-drugs and the like, which encounter stability problems when combined with free fatty acids. Preferred compositions of the invention are those containing testosterone undecanoate (TU).

DETAILED DESCRIPTION OF THE INVENTION

As used herein and in the claims, the terms "drug" and "active ingredient" are used synonymously to refer to pharmaceutical compounds or molecular structures. When used within the context of the invention, the terms refer to pharmaceutical compounds which can be used in association with the liquid carrier of the invention to produce the resulting pharmaceutical composition.

The phrase "substantially free from free fatty acid" as used within the context of describing the pharmaceutical compositions according to the invention is intended to mean that the liquid carrier contains less than 1% by weight of fatty acids that are not esterified to a polyol such as glycol.

The invention includes a liquid pharmaceutical composition comprising a drug dissolved in a liquid vehicle, the liquid vehicle comprising:

a) a glyceride of a long chain fatty acid having a chain containing from 14 to 22 carbon atoms and is present in an amount from about 15% to about 70% by weight, preferably from about 15% to about 60% by weight of said vehicle; and b) a lipophilic surfactant having an HLB of less than 10 and present in an amount of from about 30% to about 60% by weight of said vehicle.

The composition according to the invention contains a liquid vehicle which is substantially free from free fatty acids and preferably contains less than 10% by weight ethanol.

The composition can further comprise a hydrophilic surfactant, which can be present in an amount of from about 0% to about 35% by weight of the vehicle.

Suitable drugs or active ingredients which can be used in the invention are those which encounter stability problems in the presence of free fatty acids. Such drugs or pro-drugs include, but are not limited to, compounds containing ester groups which can result in transesterification, compounds containing amide groups, compounds containing alcohol groups which can result in ester formation, and compounds which contain amine groups which can result in amide formation. Examples of such drugs or active ingredients include testosterone undecanoate, hydroxyprogesterone hexanoate and other steroid esters, retinyl palmitate, fenofibrate, halofantrine, retinol and tocopherol. Preferred compositions of the invention are those containing testosterone undecanoate as the active ingredient.

Suitable long chain ($C_{14}$–$C_{22}$) triglycerides for use in the invention include, but are not limited to, arachis oil, soya bean oil, castor oil, corn oil, safflower oil, olive oil, apricot kernel oil, sesame oil, cotton seed oil, sunflower seed oil, palm oil and rapeseed oil. The triglycerides are present in amounts of from about 15% to about 70% by weight of the liquid vehicle, preferably in the amount of from about 40% to about 60% by weight of the liquid vehicle.

Suitable long chain mono-glycerides which can be used include glyceryl mono-oleate.

Suitable lipophilic surfactants for use in the invention are those having an HLB value of less than 10 (HLB<10). Lipophilic surfactants having an HLB of less than 10 which can be used include, but are not limited to: mono- and di-glycerides of fatty acids; acetic, succinic, lactic, citric and tartaric esters of mono- and di-glycerides of fatty acids; propylene glycol mono- and di-esters of fatty acids; polyglycerol esters of fatty acids; castor oil and hydrogenated castor oil ethoxylates; acid and ester ethoxylates; sorbitan esters of fatty acids; unsaturated polyglycolized glycerides, alcohol ethoxylates; and polyoxyethylene-polyoxypropylene co-polymers and block co-polymers.

Examples of mono- and di-glycerides of fatty acids which can be used as the lipophilic surfactant include, for example, glyceryl mono/di-caprylate, glyceryl mono-di-caprylate/caprate, glyceryl mono-caprylate, glyceryl mono-stearate, glyceryl mono-/di-ricinoleate, glyceryl caprylate/caprate, glyceryl mono-oleate, glyceryl dilaurate and glyceryl monostearate Acetic, succinic, lactic, citric and/or tartaric esters of mono- and/or di-glycerides of fatty acids which can be used as the lipophilic surfactant include distilled acetylated monoglycerides, caprylic/capric diglyceryl succinate, mono/di-succinylated monoglycerides, glyceryl stearate citrate, glyceryl monostearate/citrate/-lactate, glyceryl cocate/citrate/lactate.

Propylene glycol mono- and/or di-esters of fatty acids which can be used include, for example, lauroglycol (propylene glycol monolaurate) and propylene glycol dicaprylate/dicaprate.

Polyglycerol esters of fatty acids suitable as the lipophilic surfactant include polyglyceryl oleate.

Castor oil or hydrogenated castor oil ethoxylates having low ethoxylate content and HLB less than 10 can also be used, for example, 5 moles of ethylene oxide reacted with 1 mole of castor oil.

Acid and ester ethoxylates formed by reacting ethylene oxide with fatty acids or glycerol esters of fatty acids which can be used include, polyoxyethylene (4) lauric acid, polyoxyethylene (2) stearic acid, polyoxyethylene (3) stearic acid, glyceryl 12 EO dioleate.

Sorbitan esters of fatty acids suitable for use as the lipophilic surfactant include, for example, sorbitan monolaurate, sorbitan monoleate, sorbitan trioleate, sorbitan tristearate.

Examples of unsaturated polyglycolized glycerides include polyoxyethylated apricot kernel oil, polyoxyethylated corn oil, polyoxyethylated hydrogenated oil.

Alcohol ethoxylates which can be used include polyoxyethylated (3) oleyl ether, polyoxyethylated (2) oleyl ether.

Examples of polyoxyethylene-polyoxypropylene co-polymers and block co-polymers can also be used as the lipophilic surfactant.

The lipophilic surfactant is used in an amount ranging from about 30% to about 60% by weight, typically from about 40% t about 60% by weight of the liquid vehicle.

Preferred lipophilic surfactants for use in the liquid vehicle are propylene glycol mono- and/or di-esters of fatty acids. Most preferred is lauroglycol (propylene glycol monolaurate) as the lipophilic surfactant.

In a further embodiment, a pharmaceutically acceptable hydrophilic surfactant having an HLB value greater than 10 (HLB>10) can be used in addition to the long chain glyceride and lipophilic surfactant ingredient of the present invention. Examples of hydrophilic surfactants which can be used include:

a) Phospholipids, in particular lecithins, preferably soyabean lecithins.

b) Polyoxyethylene sorbitan fatty acid derivatives, for example, polyoxyethylene (20) monolaurate, polyoxyethylene (20) monopalmitate, polyoxyethylene (20) monopalmitate, polyoxyethylene (20) sorbitan monostearate, and polyoxyethylene (20) monooleate c) Castor oil or hydrogenated castor oil ethoxylates, for example, polyoxyethylene (35) castor oil, polyoxyethylene (40) hydrogenated castor oil, polyoxyethylene (40) castor oil and polyoxyethylene (60) hydrogenated castor oil.

d) Fatty acid ethoxylates, for example, polyoxyethylene (8) stearate, polyoxyethylene (30) monolaurate, polyoxyethylene (20) stearate, polyoxyethylene (15) oleate.

e) Alcohol ethoxylates, for example, polyoxyethylene (10) oleyl ether, polyoxyethylene (30) oleyl ether, polyoxyethylene (20) $C_{12}$–$C_{14}$ fatty ether.

f) Polyoxyethylene-polyoxypropylene co-polymers and block co-polymers.

g) Alkylphenol surfactants, for example, polyoxyethylene (9–10) nonylphenol, polyoxyethylene (9) nonylphenol.

h) Saturated polyglycolized medium chain triglycerides, for example, a combination of glyceryl caprylate and polyethylene glycol (8) caprylate/caprate.

The compositions can contain up to 40% by weight of hydrophilic surfactant based on the weight of the liquid vehicle.

Other conventional ingredients or additives can be used in the compositions in accordance with the invention. For example, anti-oxidants such as d-alpha-tocopherol, BHA, BHT and co-solvents such as ethanol, diethylene glycol monoethylether, plasticizers such as propylene glycol, and the like.

Compositions according to the invention can be prepared using conventional methods such as those described in Lacy et al., Patent Cooperation Treaty WO95/24893 published Sep. 21, 1995. A typical process form preparing carrier systems of the invention begins with weighing out the oil component into a suitable stainless steel vessel and then weighing the lipophilic surfactant and adding it to the container. Mixing of the two liquids is effected by the use of a homogenizing mixer or other high shear device. If the material is solid at room temperature, sufficient heat is applied to ensure fluidity without chemical decomposition. If used, the hydrophilic surfactant is added to the other two components. If a hydrophilic solvent is used it is added last with mixing. The drug is then weighed and added to the combined liquids and mixing continued until either a homogenous solution or suspension is prepared. The formulation is then de-aerated before encapsulation in either soft or hard capsules. In some instances, the fill formulation may be held at elevated temperature using a suitable jacketed vessel to aid processing.

The compositions can be encapsulated in softgel or hard shell capsules. Methods of softgel encapsulation are taught in *Theory and Practice of Industrial Pharmacy* (Lachman & Leiberman, $2^{nd}$ Edition, publ. Henry Kimpton Publishers, London). Methods of liquid-fill hardshell encapsulation are disclosed in *Hardcapsules-Development and Technology*, edited by K. Ridgeway, (published by Pharmaceutical Press) (1987).

The invention will now be illustrated by the following Examples, which are not intended to be construed as limitations to the invention:

EXAMPLES

Examples 1A Through 14A

Preparation of Liquid Vehicle Formulations

Fourteen liquid vehicle formulations were prepared as measured in parts by weight and contained the following respective ingredients:

| Example: | Ingredients: | % (w/w): |
|---|---|---|
| 1 | Soya Bean oil | 15 |
|   | Lauroglycol | 60 |
|   | Polyoxyethylene (20) monopalmitate | 25 |
| 2 | Arachis oil | 25 |
|   | Lauroglycol | 40 |
|   | Polyoxyethylene (20) monopalmitate | 35 |
| 3 | Arachis oil | 40 |
|   | Lauroglycol | 60 |
| 4 | Arachis oil | 40 |
|   | Glyceryl mono-oleate | 60 |
| 5 | Castor oil | 60 |
|   | Lauroglycol | 40 |
| 6 | Soya Bean oil | 50 |
|   | Lauroglycol | 50 |
| 7 | Soya Bean oil | 20 |
|   | Glyceryl mono/di-caprylate | 50 |
|   | Glyceryl caprylate and polyethylene glycol (8) caprylate/caprate | 30 |
| 8 | Castor oil | 60 |
|   | Glyceryl mono/di-caprylate | 40 |
| 9 | Castor oil | 40 |
|   | Lauroglycol | 55 |
|   | Ethanol | 5 |
| 10 | Castor oil | 30 |
|   | Glyceryl mono/di-caprylate | 40 |
|   | Polyoxyethylene (35) castor oil | 30 |
| 11 | Castor oil | 50 |
|   | Lauroglycol | 30 |
|   | Glyceryl caprylate and polyethylene glycol (8) caprylate/caprate | 20 |
| 12 | Arachis oil | 40 |
|   | Glyceryl mono-oleate | 30 |
|   | Polyoxyethylene (35) castor oil | 25 |
|   | Ethanol | 5 |
| 13 | Arachis oil | 25 |
|   | Lauroglycol | 60 |
|   | Glyceryl caprylate and polyethylene glycol (8) caprylate/caprate | 15 |
| 14 | Arachis oil | 60 |
|   | Glyceryl mono/di-caprylate | 40 |

Examples 1B Through 14B

Preparation of Pharmaceutical Compositions Containing Liquid Vehicle Formulations Compositions containing an active ingredient and liquid vehicle were prepared by mixing 88 parts by weight of each liquid vehicle formulation as prepared in Examples 1A through 14A together with 12 parts by weight of testosterone undecanoate (TU). The resulting composition contained testosterone undecanoate in stable form which was suitable for encapsulation in the preparation of softgel capsules.

Example 15

Comparative Stability Test of Testosterone Undecanoate (TU)

Accelerated stability trials were conducted using pharmaceutical compositions containing testosterone undecanoate as the active ingredient in samples using the liquid vehicle according to the invention and a liquid vehicle control sample.

Five samples containing testosterone undecanoate were prepared in accordance with the formulations depicted in Examples 1B through 5B. The control sample containing testosterone undecanoate in combination with oleic acid was prepared. All six samples were then stored for a period of three months.

Following the three month period, each of the resulting samples was analyzed for testosterone undecanoate content. The five samples containing composition prepared according to the invention were found to contain at least 86% and even at least 90% of the active ingredient, whereas the control sample was found to contain less than 70% of the original testosterone undecanoate content.

In conclusion, the data demonstrates that the samples prepared according to the invention exhibited an increased longevity of the original active ingredient (i.e., testosterone undecanoate) in storage when compared to the control sample containing the active ingredient with oleic acid.

Industrial Applicability

The invention is useful in the production of pharmaceutical compositions for oral administration wherein the drug or active ingredient is known to have stability problems associated with the use of free fatty acids. Examples of such drugs or active ingredients include sex hormones such as testosterone undecanoate. The compositions of the invention enhance the solubility of such compounds and improve the storage stability thereof, and can be advantageously used in soft gel and hard shell capsular formulations.

The complete disclosures of all patents, patent applications, and publications are incorporated herein by reference as if each were individually incorporated by reference. The invention has been described with reference to various specific and preferred embodiments and techniques. However, it should be understood that many variations and modifications may be made while remaining within the spirit and scope of the invention.

We claim:

1. A liquid pharmaceutical composition having a drug dissolved in a liquid vehicle, said liquid vehicle consisting essentially of:
   a) a glyceride of a long chain fatty acid;
   b) a lipophilic surfactant having an HLB of less than 10; and wherein said liquid vehicle is substantially free from free fatty acid.

2. A liquid pharmaceutical composition according to claim 1, wherein the drug is testosterone undecanoate.

3. The liquid pharmaceutical composition according to claim 1, wherein the glyceride of a long chain fatty acid is present in an amount from about 15% to about 70% by weight in the liquid vehicle, and wherein the lipophilic surfactant is present in an amount from about 30% to about 60% by weight in the liquid vehicle.

4. The liquid pharmaceutical composition according to claim 1, wherein the glyceride is a long chain triglyceride having 14 to 22 carbon atoms.

5. The liquid pharmaceutical composition according to claim 4, wherein the long chain triglyceride is selected from the group consisting of arachis oil, soya bean oil, castor oil, corn oil, safflower oil, olive oil, apricot kernel oil and sesame oil, and combinations thereof.

6. The liquid pharmaceutical composition according to claim 1, wherein the glyceride of a long chain fatty acid is a mono- or diglyceride.

7. The liquid pharmaceutical composition according to claim 6, wherein the glyceride of a long chain fatty acid is the monoglyceride glyceryl mono-oleate.

8. The liquid pharmaceutical composition according to claim 1, wherein the lipophilic surfactant is selected from the group consisting of: mono- and diglycerides of fatty acids; acetic, succinic, lactic and tartaric esters of mono- and di-glycerides of fatty acids; propylene glycol mono- and di-esters of fatty acids; castor oil and hydrogenated castor oil ethoxylates; acid and ester ethoxylates; sorbitan esters of fatty acids; unsaturated polyglycolized glycerides; alcohol ethoxylates; and polyoxyethylene-propylene co-polymers and block co-polymers, and combinations thereof.

9. The liquid pharmaceutical composition according to claim 8, wherein the lipophilic surfactant is a propylene glycol mono-ester of a fatty acid.

10. The liquid pharmaceutical composition according to claim 9, wherein the lipophilic surfactant is lauroglycol.

11. A soft gel capsule containing the liquid pharmaceutical composition according to claim 1.

12. A hard shell capsule containing the liquid pharmaceutical composition according to claim 1.

13. The liquid pharmaceutical composition according to claim 1, further comprising ethanol.

14. The liquid pharmaceutical composition according to claim 13 which contains less than 15% by weight ethanol.

15. A liquid pharmaceutical composition for oral administration having testosterone undecanoate dissolved in a liquid vehicle, said liquid vehicle consisting essentially of:
   a) a glyceride of a long chain fatty acid having from 14 to 22 carbon atoms; and
   b) lauroglycol.

16. The liquid pharmaceutical composition according to claim 15, wherein the glyceride of a long chain fatty acid is a triglyceride.

17. A soft gel capsule containing the liquid pharmaceutical composition according to claim 15.

18. A hard shell capsule containing the liquid pharmaceutical composition according to claim 15.

* * * * *